(12) United States Patent
Fu

(10) Patent No.: US 9,666,893 B2
(45) Date of Patent: May 30, 2017

(54) HYDROTHERMAL TREATMENT METHOD FOR PRODUCING REDOX-ACTIVE TRANSITION METAL COORDINATION COMPOUNDS

(71) Applicant: Cristal Inorganic Chemicals Switzerland Ltd, Baar (CH)

(72) Inventor: Guoyi Fu, Glenwood, MD (US)

(73) Assignee: Cristal Inorganic Chemicals Switzerland Ltd, Baar (CH)

(*) Notice: Subject to any disclaimer, the term of this patent is extended or adjusted under 35 U.S.C. 154(b) by 15 days.

(21) Appl. No.: 14/813,372

(22) Filed: Jul. 30, 2015

(65) Prior Publication Data

US 2017/0033388 A1    Feb. 2, 2017

(51) Int. Cl.

| | |
|---|---|
| *H01M 8/18* | (2006.01) |
| *H01M 8/20* | (2006.01) |
| *C07C 37/66* | (2006.01) |
| *C07F 7/28* | (2006.01) |
| *H01M 8/08* | (2016.01) |

(52) U.S. Cl.
CPC .............. *H01M 8/188* (2013.01); *H01M 8/20* (2013.01); *C07C 37/66* (2013.01); *C07F 7/28* (2013.01); *H01M 8/08* (2013.01); *H01M 2300/0002* (2013.01)

(58) Field of Classification Search
CPC .......... C07C 37/66; C07F 7/28; H01M 8/188; H01M 8/08; H01M 8/20
See application file for complete search history.

(56) References Cited

U.S. PATENT DOCUMENTS

| | | | |
|---|---|---|---|
| 8,691,413 B2 | 4/2014 | Esswein et al. | |
| 8,753,761 B2 | 6/2014 | Esswein et al. | |
| 2002/0000532 A1* | 1/2002 | Takahashi | C01G 23/00 252/1 |
| 2014/0138576 A1 | 5/2014 | Esswein et al. | |

OTHER PUBLICATIONS

Marie, Helene., et al., "PEM Anchorage on Titanium Using Catechol Grafting," XP-002760855, Nov. 2012, vol. 7, Issue 11, e50326, PLOS ONE, Paris, France.

Song, Jae-Sung., et al., "Photonic decomposition of ultrafine, rutile phased $TiO_2$ powder in aqueous 4-chlorophenol solutions," XP-002760854, Smart Material Structures 15(2006), pp. S65-S73, Institute of Physics Publishing, Korea.

Magers, Keith D., et al., "Polarographic and Spectroscopic Studies of the Manganese(II), -(III), and -(IV) Complexes Formed by Polyhydroxy Ligands", Inorganic Chemistry, Mar. 1978, pp. 515-523, 17(3), Univ. of California Dept. of Chem., Riverside.

Sofen, Stephen R., et al., "Crystal and Molecular Structures of Tetrakis(catecholato)hafnate(IV) and -cerate(IV). Further Evidence for a Ligand Field Effect in the Structure of Tetrakis(catecholate)uranate(IV)", Inorganic Chemistry, 1979, pp. 1611-1616, 18(6), Univ. of California Dept. of Chem., Berkeley.

Cooper, Stephen R., et al., "Synthetic, Structural, and Physical Studies of Bis(triethylammonium) Tris(catecholato)vanadate(IV), Potassium Bis(catecholato)oxovanadate(IV), and Potassium Tris(catecholato)vanadate(III)", Journal of the American Chemical Society, 1982, pp. 5092-5102, 104, Harvard Univ. Dept. of Chem., Cambridge.

Borgias, Brandan A., et al., "Synthetic, Structural, and Physical Studies of Titanium Complexes of Catechol and 3,5-Di-*tert*-butylcatechol", Inorganic Chemistry, 1984, pp. 1009-1016, 23, Univ. of California Dept. of Chem., Berkeley.

Davies, Julian A., et al., "Electroceramics from Source Materials via Molecular Intermediates: $BaTiO_3$ from $TiO_2$ via $(Ti(catecholate)_3)^{2-}$", Journal of the American Ceramic Society, 1990, pp. 1429-1430, 73(5), Univ. of Toledo Dept. of Chem., Toledo.

Buettner, Katherine M., et al., "Bioinorganic Chemistry of Titanium", Chemical Reviews, 2012, pp. 1863-1881, 112, Yale Univ. Dept. of Chem., New Haven.

* cited by examiner

*Primary Examiner* — Ladan Mohaddes

(57) ABSTRACT

A method for producing an aqueous electrolyte comprising a redox-active coordination compound of a transition metal which comprises reacting an oxide of the corresponding transition metal in an aqueous reaction medium with a chelating agent in a hydrothermal reaction zone at a temperature in the range of from 100° C. to 160° C. for a period of from 4 hours to 48 hours.

5 Claims, 1 Drawing Sheet
(1 of 1 Drawing Sheet(s) Filed in Color)

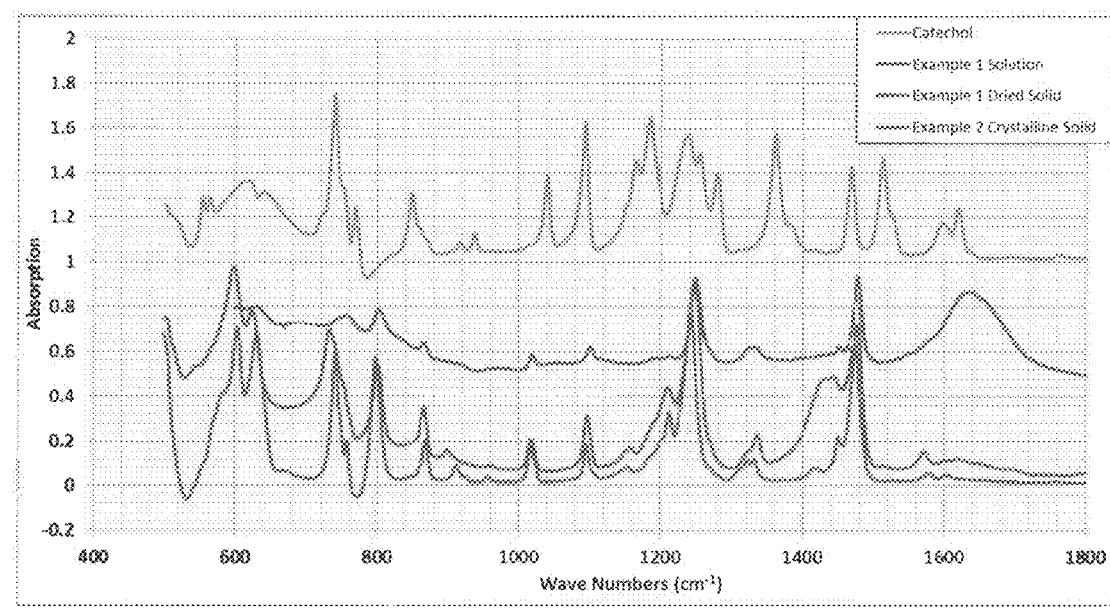

HYDROTHERMAL TREATMENT METHOD FOR PRODUCING REDOX-ACTIVE TRANSITION METAL COORDINATION COMPOUNDS

BACKGROUND OF THE INVENTION

The presently described and claimed inventive concept(s) relate to a method for producing electrolytes for electrochemical energy storage systems, and, more particularly, to a method for producing redox-active Ti(IV) coordination compounds in aqueous solution for use as electrolytes in flow battery systems.

A flow battery is a rechargeable fuel cell in which an electrolyte containing one or more dissolved electroactive elements flows through an electrochemical cell that reversibly converts chemical energy directly to electricity. Modern flow batteries are generally two electrolyte systems in which the two electrolytes, acting as liquid energy carriers, are pumped simultaneously through two half-cells separated by a membrane which comprise the reaction cell. On charging, supplied electrical energy causes a chemical reduction reaction in one electrolyte and an oxidation reaction in the other. A generally thin ion exchange membrane positioned between the half-cells prevents the electrolytes from mixing but allows selected ions to pass through to complete the redox reaction. On discharge the chemical energy contained in the electrolyte is released in the reverse reaction, and electrical energy can be drawn from the electrodes. When in use the electrolytes are continuously pumped in a circuit between reactor and storage tanks.

U.S. Pat. No. 8,753,761 B1 describes aqueous redox flow batteries which comprise metal ligand coordination compounds as a novel class of flow battery materials. Metal ligand coordination compounds, such as those comprising titanium, have been observed to exhibit high solubility, reversible electrochemistry (e.g., rapid electrochemical kinetics) and tunable redox potentials.

Production methods for Ti(IV) coordination compounds that can be used as electrolytes in flow batteries normally involve using precursors, such as, for example, $TiCl_4$, titanium alkoxides, and the like as starting materials. These precursors are reacted with the corresponding complexing agents in water or a solvent. However, these precursor materials are all highly reactive and can be difficult to handle especially at large production scale. In addition, counter ions and by-products (e.g., chloride, alcohols, etc.) that are generated during the production process need to be separated and treated which tends to add significant cost to a commercial production process. Thus, the need exists for an improved more economical method for producing redox-active Ti(IV) coordination compounds of the type which are useful in electrochemical energy storage systems, and particularly in flow battery systems.

SUMMARY OF THE INVENTION

The described and claimed inventive concepts(s) comprise in one embodiment a method for producing redox-active coordination compounds of transition metals, such as titanium, iron, vanadium, manganese, cerium, and uranium. According to another embodiment, the inventive concept(s) comprises a method for producing Ti(IV) coordination compounds of the type which are useful in electrochemical energy storage systems, and particularly in flow battery systems. The method comprises reacting $TiO_2$ (or the corresponding oxide of the desired transition metal) in an aqueous reaction medium directly with a chelating agent, or with a combination of chelating agents, in a hydrothermal reaction zone at a temperature in the range of from 100° C. to 160° C. for a period of time from 4 hours up to 48 hours. This process typically results in a clear solution of the coordination compound, which may be used directly as an electrolyte solution in a flow battery. In the event that a solid product is desired, it may be produced by cooling a saturated solution, for example, in a refrigerator. A saturated solution may be achieved by evaporation of a solution of the coordination compound using an evaporator According to another embodiment, the chelating agent can be selected from the group consisting essentially of catechol, pyrogallol, 2,3-naphthalenediol, other aromatic 1,2-diols, ascorbic acid, and glyconic acid, or from a combination thereof.

The aqueous solution of the corresponding redox-active Ti(VI) coordination compound can be deployed directly as an electrolyte in a flow battery. The reaction is clean without any undesirable by products or counter ions that would affect the functionality of the electrolyte. The raw materials are stable and easy to handle.

The described and claimed inventive concept(s) also include a method for preparing coordination compounds of other transition metals, such as, for example, aluminum, chromium, iron, vanadium, manganese, cerium, and uranium, by reacting the corresponding metal oxide with one or more chelating agents listed above under corresponding hydrothermal conditions.

The described and claimed inventive concept(s) comprise lower cost (i.e., more economical) methods for obtaining Ti(IV) coordination compounds in aqueous solution than are currently known in the art without having to manage removal of undesirable counter ions and by-products.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1 is a comparison of FT-IR spectra of titanium catechol complexes and a catechol sample

DETAILED DESCRIPTION OF THE INVENTION

The described and claimed inventive concepts(s) comprise a method for producing redox-active coordination compounds of transition metals, and particularly Ti(IV) coordination compounds, in aqueous solution which are useful in electrochemical energy storage systems, and particularly in flow battery systems. Transition metals other than titanium which are operable according to the described method include aluminum, chromium, iron, vanadium, manganese, cerium, and uranium.

However, before explaining the inventive concept(s) in detail, it is to be understood that the presently disclosed and claimed inventive concept(s) is not limited in its application to the details of construction and the arrangement of the components or steps or methodologies set forth in the following description or illustrated in the drawings. The results obtainable from the presently disclosed and claimed inventive concept(s) are capable of being achieved, practiced or carried out in various ways. Also, it is to be understood that the phraseology and terminology employed herein is for the purpose of description and should not be regarded as limiting.

Unless otherwise defined herein, technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. For example, the term "titanium dioxide" as used herein is intended to mean and include titanium oxide and titania and any of the various forms of titanium dioxide.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed and claimed herein can be made and executed without undue experimentation in light of the present disclosure. While the articles and methods of the presently disclosed and claimed inventive concept(s) have been described in terms of particular embodiments, it will be apparent to those of skill in the art that variations may be applied to the articles and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the presently disclosed and claimed inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The method embraced within the inventive concept(s) described herein comprises a hydrothermal method for easily and conveniently synthesizing coordination compounds of transition metals which include titanium, aluminum, chromium, iron, vanadium, manganese, cerium, and uranium.

For producing electrolytes comprising redox-active Ti(IV) coordination compounds, the method begins with $TiO_2$ as the starting material and directly reacts it with one or more complexing or chelating agents under hydrothermal conditions.

Using the sodium salt of titanium catecholate complex as an example, the reaction is shown in Equation (1):

$$TiO_2 + 3C_6H_4(OH)_2 + 2NaOH \rightarrow Ti(C_6H_4O_2)_3^{2-} + 2Na^+ + 4H_2O \quad (1)$$

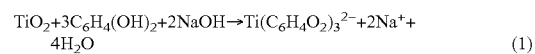

The product is an aqueous solution as the sodium salt that is highly soluble in water. The concentration of the solution may be adjusted up to 50 wt % as the sodium salt of the complex. If a higher concentration is desired, it can be achieved by removing some of the solvent (water) using an evaporator.

The crystalline solids of the complex may also be obtained as an ammonium or a potassium salt. Taking the ammonium salt as an example, the reaction is shown in Equation (2):

$$TiO_2 + 3C_6H_4(OH)_2 + 2NH_4OH \rightarrow (NH_4)_2Ti(C_6H_4O_2)_3 + 4H_2O \quad (2)$$

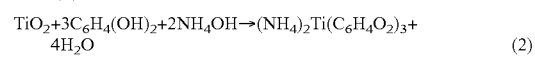

If desired, the crystalline solids obtained as the reaction product can be separated by filtration, centrifugation, and/or by other convenient separation methods.

Since it is known that $Ti(C_6H_4O_2)_3^{2-}$ has a formation constant of $10^{60}$, the reaction is highly favorable thermodynamically. Hydrothermal conditions as described and claimed herein provide enough energy to make the reaction kinetically favorable.

Most notably according to the described and claimed inventive concept(s) is that the coordination reaction is clean and without any undesirable by products. The method may be used for synthesizing similar coordination compounds of other transition metals, such as, for example, aluminum, chromium, iron, vanadium, manganese, cerium, and uranium.

The following Examples are provided to illustrate certain embodiments described within this disclosure. While each of the Examples is considered to describe specific individual embodiments of the method of preparation and results achieved, none of the Examples should be considered to limit the more general embodiments described herein.

Example 1—Preparation of Titanium Catechol Complex, Sodium Salt 208.1 g catechol (Alfa Aesar) was dissolved in 800 g deionized water, to which 120 g of NaOH solution containing 50.1 g NaOH and 58.8 g of a $TiO_2$ product containing 50 g $TiO_2$ (the product contained 85% TiO2 with the rest being water) were added consecutively. After a short mixing period of from 3 to 5 minutes the mixture was transferred to a two-liter hydrothermal reactor, and the reaction mixture was treated, i.e., raised to a temperature of 120° C. and held at that temperature for 16 hours. Thereafter, the hydrothermal reactor was cooled to room temperature or ambient temperature, and a dark brown, clear solution was obtained. The $TiO_2$ was completely dissolved during the treatment period, due to the formation of the soluble catechol complex. Chemical analysis showed the solution contained about 22 wt % of the titanium catechol complex compound. The major FT-IR bands of the solution and an oven dried sample of the solution matched those published in the literature (as shown in FIG. 1) indicating the desired compound was indeed formed by this hydrothermal synthesis method.

Example 2—Preparation of Titanium Catechol Complex, Ammonium Salt

The same procedure was followed as in Example 1 except that the NaOH solution was replaced with 72.5 g of an ammonia solution (containing 29 wt % $NH_3$). After hydrothermal treatment, the reaction mixture was transferred to a beaker and stored in a refrigerator overnight for crystallization. Crystals that were formed were separated by filtration. FT-IR spectrum of the sample showed absorption bands in agreement with that of the ammonium salt of titanium catechol complex published in the literature.

Example 3—Preparation of Titanium Pyrogallol Complex, Ammonium Salt

The same procedure was followed as in Example 2 except that an equivalent amount of pyrogallol was used in place of catechol. Hydrothermal treatment of the reaction mixture resulted in a clear, dark brown solution similar to the titanium catechol complex. The ammonium salt of the titanium pyrogallol complex that was formed showed higher solubility in water than the corresponding catechol complex. The solution didn't crystallize even after being stored in a refrigerator overnight. A solid sample was obtained by vacuum evaporation.

Example 4—Preparation of Vanadium Catechol Complex, Potassium Salt 66.7 g catechol was dissolved in 600 g deionized water and 39.6 g KOH was added. After the KOH had dissolved, 18.2 g $V_2O_5$ was added. The reaction mixture was then transferred to a two-liter hydrothermal reactor and treated, i.e., raised to a temperature of 120° C. and held at that temperature for 16 hours. The treatment produced a clear, dark brown solution similar to the titanium catechol complex. Cooling in a refrigerator didn't result in crystallization. A solid sample was obtained by vacuum evaporation.

As those skilled in the art will appreciate, numerous modifications and variations of the described and claimed inventive concept(s) are possible in light of these teachings, and all such are contemplated hereby. The present invention contemplates and claims those inventions that may result from the combination of features described herein and those of the cited prior art references which complement the features of the present invention.

What is claimed is:

1. A method for producing an aqueous electrolyte comprising a redox-active coordination compound of a transition metal wherein the transition metal is titanium which comprises reacting an oxide of the transition metal in an aqueous reaction medium with a chelating agent selected from the group consisting essentially of catechol, pyrogallol, 2,3-naphthalenediol, ascorbic acid, and glyconic acid, or with a combination of such chelating agents in a hydrothermal reaction zone at a temperature in the range of from 100° C. to 160° C. for a period of time from 4 hours to 48 hours to yield said aqueous electrolyte.

2. The method of claim 1 which includes the additional step of cooling the aqueous electrolyte with the result that a crystalline solid is formed, and recovering the crystalline solid.

3. The method of claim 1 or claim 2 wherein said transition metal is selected from the group comprising titanium, aluminum, chromium, iron, vanadium, manganese, cerium, and uranium and said chelating agent is selected from the group consisting essentially of aromatic 1,2-diols and combinations of such diols.

4. A method for producing an aqueous electrolyte comprising a redox-active Ti(IV) coordination compound which comprises reacting $TiO_2$ in an aqueous reaction medium with a chelating agent selected from the group consisting essentially of catechol, pyrogallol, 2,3-naphthalenediol, ascorbic acid, glyconic acid, and combinations thereof in a hydrothermal reaction zone at a temperature in the range of from 100° C. to 160° C. for a period of time from 4 hours to 48 hours.

5. A method for producing an aqueous electrolyte comprising a redox-active coordination compound of a transition metal selected from the group comprising titanium, aluminum, chromium, iron, vanadium, manganese, cerium, and uranium which comprises reacting an oxide of the corresponding transition metal in an aqueous reaction medium with a chelating agent selected from the group consisting essentially of aromatic 1,2-diols and combinations of such diols in a hydrothermal reaction zone at a temperature in the range of from 100° C. to 160° C. for a period of time from 4 hours to 48 hours.

* * * * *